United States Patent
Umemoto et al.

(10) Patent No.: US 8,282,864 B2
(45) Date of Patent: Oct. 9, 2012

(54) WATER-RESISTANT POLARIZING FILM, AND PROCESS FOR PRODUCING THE SAME

(75) Inventors: Toru Umemoto, Ibaraki (JP); Sadahiro Nakanishi, Ibaraki (JP); Tadayuki Kameyama, Ibaraki (JP)

(73) Assignee: Nitto Denko Corporation, Ibaraki-shi (JP)

( * ) Notice: Subject to any disclaimer, the term of this patent is extended or adjusted under 35 U.S.C. 154(b) by 0 days.

(21) Appl. No.: 13/146,863

(22) PCT Filed: Oct. 5, 2009

(86) PCT No.: PCT/JP2009/005138
§ 371 (c)(1),
(2), (4) Date: Jul. 28, 2011

(87) PCT Pub. No.: WO2010/092637
PCT Pub. Date: Aug. 19, 2010

(65) Prior Publication Data
US 2011/0284810 A1    Nov. 24, 2011

(30) Foreign Application Priority Data
Feb. 13, 2009    (JP) ................... 2009-030620

(51) Int. Cl.
  *F21V 9/14*   (2006.01)
  *G02B 5/30*   (2006.01)
  *G02C 7/12*   (2006.01)
  *G02B 5/22*   (2006.01)
  *G02B 5/23*   (2006.01)

(52) U.S. Cl. ........ 252/585; 252/586; 252/587; 359/350; 359/885; 428/1.3; 428/212; 430/7; 430/270.1

(58) Field of Classification Search ............... 252/585, 252/586, 587; 264/1.35; 427/163.1, 163.2; 534/577, 832; 106/287.26; 359/350, 885; 428/1.3, 212; 430/7, 270.1
See application file for complete search history.

(56) References Cited

U.S. PATENT DOCUMENTS
2004/0009414 A1    1/2004   Araki

FOREIGN PATENT DOCUMENTS
| JP | 8-302325    | * | 11/1996 |
| JP | 11-021538   | * | 1/1999  |
| JP | 11-21538    | A | 1/1999  |
| JP | 2004-86139  | A | 3/2004  |
| JP | 2004-126193 | A | 4/2004  |
| JP | 2004-139050 | A | 5/2004  |
| JP | 2004-300339 | * | 10/2004 |
| JP | 2006-323377 | A | 11/2006 |
| JP | 2007-126628 | A | 5/2007  |
| JP | 2009-199075 | A | 9/2009  |

OTHER PUBLICATIONS
International Search Report for PCT/JP2009/005138, mailing date of Jan. 12, 2010.

* cited by examiner

*Primary Examiner* — Bijan Ahvazi
(74) *Attorney, Agent, or Firm* — Westerman, Hattori, Daniels & Adrian, LLP

(57) ABSTRACT

There is provided a water-resistant polarizing film including an organic dye having at least two anionic groups, and an alicyclic structure-containing compound having at least two nitrogen atoms in a molecule. Examples of the organic dye typically include an azo compound represented by the following general formula (2):

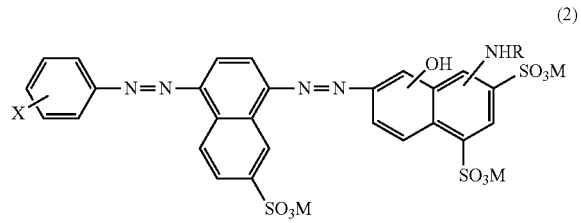

(2)

6 Claims, No Drawings

WATER-RESISTANT POLARIZING FILM, AND PROCESS FOR PRODUCING THE SAME

BACKGROUND OF THE INVENTION

1. Field of the Invention

The present invention relates to a water-resistant polarizing film and a process for producing thereof.

2. Description of the Related Art

Conventionally, a water-resistant organic thin film including an organic compound having at least two sulfonic acid groups and a compound having at least two nitrogen atoms in a molecule is well known (for example, Japanese Patent Application Laid-Open Publication No. JP 11-21538 A). Aromatic ring structure-containing compounds, such as 4,4'-dipyridine and melamine (the following formula (1)) or the like have been used as the aforementioned compound having at least two nitrogen atoms in the molecule.

[Chemical formula 1]

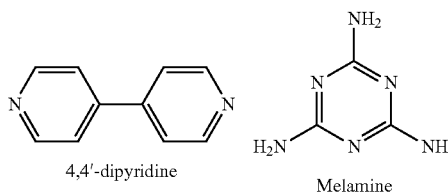

4,4'-dipyridine

Melamine (1)

A water-resistant polarizing film including such an aromatic ring structure-containing compound is, however, has insufficient water resistance and suffers from a problem that optical characteristics, such as a transmittance and a polarizing degree or the like become deteriorated when exposed to a humid environment for a long period of time.

SUMMARY OF THE INVENTION

It is an object of the present invention to provide a water-resistant polarizing film having superior water resistance to conventional ones and a process for producing thereof.

Effects of an alicyclic structure-containing compound having at least two nitrogen atoms in a molecule which exert on water resistance of a polarizing film will now be described as below.

(a) Need for a Compound Having at Least Two Nitrogen Atoms

A water-resistant polarizing film is obtained by contacting a compound having one or more nitrogen atoms with an organic dye having one or more anionic groups to react the anionic groups with the nitrogen atoms (cross-link by an ion bond). It is impossible to cross-link a plurality of organic dyes (intermolecular cross-linking) when the number of the nitrogen atom of the compound is one, which results in no increase in water resistance of the polarizing film. Since it is possible to cross-link a plurality of organic dyes when the number of the nitrogen atoms is two or more, it is possible to increase water resistance.

(b) Need for the Compound being Alicyclic-Structured

It is presumed that adjacent organic dyes are not uniformly aligned from the fact that the peak of an X-ray diffraction becomes broad when the polarizing film absorbs moisture. The aromatic ring structure-containing compound has no conformation (steric conformation), so that the distance between two nitrogen atoms in a molecule is fixed. It is impossible for the aromatic ring structure-containing compound to follow orientation changes of organic dyes in an environment where the orientation of the organic dyes easily becomes non-uniformed due to influence caused by humidity. Accordingly, the organic dyes tend to be physically separated from the aromatic ring structure-containing compound and an ion bond is easily unbound, resulting in poor water resistance. On the other hand, in the case of an alicyclic structure-containing compound, the distance between two nitrogen atoms in a molecule is changeable because some conformations exist. For instance, in the case of piperazine, it is estimated that the distance between nitrogen atoms is changed by approximately 0.02 nm. Consequently, it is possible for the alicyclic structure-containing compound to follow the changes of the orientation of the organic dyes, so that the ion bond to bond the organic dyes to the alicyclic structure-containing compound is difficult to be unbound. As a result, the alicyclic structure-containing compound is superior in water resistance and the orientation degree of the organic dyes (influences the polarization degree) is maintained.

The summary of the present invention is described as follows:

In a first preferred embodiment, a water-resistant polarizing film according to the present invention includes an organic dye having at least two anionic groups and an alicyclic structure-containing compound having at least two nitrogen atoms in a molecule.

In a second preferred embodiment of a water-resistant polarizing film according to the present invention, each of the anionic group is any one of a sulfonic acid group, a carboxyl group, a phosphate group, and a base thereof.

In a third preferred embodiment of a water-resistant polarizing film according to the present invention, the organic dye is an azo compound represented by the following general formula (2):

[Chemical formula 2]

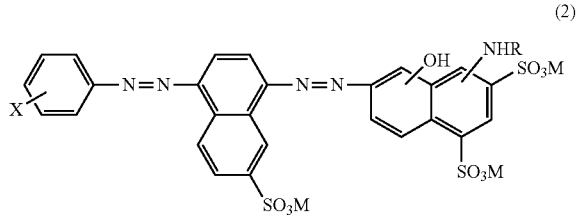

(2)

wherein R is a hydrogen atom, an alkyl group having 1 to 3 carbon numbers, an acetyl group, a substituted or unsubstituted benzoyl group, or a substituted or unsubstituted phenyl group. X is a hydrogen atom, a halogen atom, a nitro group, a cyano croup, an alkyl group having 1 to 4 carbon numbers, an alkoxy group having 1 to 4 carbon numbers or a —$SO_3M$ group. M represents a counterion.

In a fourth preferred embodiment of a water-resistant polarizing film according to the present invention, the alicyclic structure-containing compound is any one of cycloalkyl diamine, piperazine, homopiperazine, 1,4-diazabicyclo (2,2,2) octane (DABCO), and sparteine or a mixture thereof.

In a fifth preferred embodiment, a process for producing a water-resistant polarizing film according to the present invention includes a step of contacting a liquid containing an alicyclic structure-containing compound having at least two nitrogen atoms in a molecule with a polarizing film including an organic dye having at least two anionic groups.

ADVANTAGE OF THE INVENTION

In the water-resistant polarizing film of the present invention, optical characteristics, such as a transmittance and a polarization degree are more insusceptible than conventional polarizing films, even if the water-resistant polarizing film is exposed to a humid environment for a long period of time.

DESCRIPTION OF THE PREFERRED EMBODIMENTS

[Water-Resistant Polarizing Film]

A water-resistant polarizing film of the present invention includes an organic dye having at least two anionic groups and an alicyclic structure-containing compound having at least two nitrogen atoms in a molecule. Typically, it is possible to obtain the aforementioned water-resistant polarizing film by contacting a liquid containing an alicyclic structure-containing compound having at least two nitrogen atoms in a molecule with a surface of a polarizing film including an organic dye having at least two anionic groups. The liquid is hereinafter referred to as "a water-resistant treatment liquid" and the process is hereinafter referred to as "a water-resistant treatment process." In the water-resistant treatment process, the alicyclic structure-containing compound having at least two nitrogen atoms in the molecule is incorporated into the polarizing film including an organic dye having at least two anionic groups.

The water-resistant polarizing film of the present invention preferably exhibits absorption dichroism at least at one wavelength in a visible light region (at a wavelength of 380 nm to 780 nm). It is generally preferable that polarizing films have a high transmittance and a high polarization degree. According to the present invention, it is possible to obtain a polarizing film having a transmittance of 38% or higher and a polarization degree of 98% or higher. Further, the polarization degree is a value obtained from Y value whose visibility has been corrected. In the water-resistant polarizing film of the present invention, it is possible to minimize the quantity changed (absolute value) of the polarization degree to less than 2%, even when storing the polarizing film for a long period of time (for instance, 500 hours) in an environment of humidity of 90 RH %.

The thickness of the water-resistant polarizing film of the present invention is not particularly limited, but is preferably 0.1 μm to 10 μm. When the water-resistant polarizing film has a thickness of less than 1 μm, the water-resistant polarizing film may be formed on a support to secure self-reliance.

[Organic Dye]

The organic dye to be used in the present invention has at least two anionic groups in a molecule structure. Examples of the aforementioned anionic groups include a sulfonic acid group, a carboxyl group, a phosphate group, and a base thereof or the like. The number (substituted number) of anionic groups contained in the organic dye is preferably 2 to 4.

Such an organic dye acts as a substituent group to provide solubility in a hydrophilic solvent before contacting a water-resistant treatment liquid (before water-resistant treatment), so that it is easy to prepare a coating solution.

On the other hand, it is possible to obtain a superior water-resistant polarizing film after conducting water-resistant treatment by contacting the water-resistant treatment liquid with the organic dye because the anionic group acts as a cross-linking point with the alicyclic structure-containing compound having at least two nitrogen atoms in the molecule.

An organic dye described in Japanese Patent Application Laid-Open Publication Nos. JP 2007-126628 A and JP 2006-323377 A or the like may be used as the aforementioned organic dye. Such an organic dye listed in these publications exhibits liquid crystallinity in a solution state and a longitudinal axis of supramolecular aggregates may be oriented in a flow direction when applying shearing force in a liquid crystal state.

The aforementioned organic dye is preferably an azo compound represented by the general formula (2) mentioned below. Such an azo compound exhibits stable liquid crystal phases (lyotropic liquid crystallinity) in a state of being dissolved in a solvent and is excel in orientation. Further, in the aforementioned azo compound, steric hindrance among —$SO_3M$ groups becomes smaller by positioning the —$SO_3M$ groups at a specific location and the linearity of molecules before and after water-resistant treatment is maintained. As a result, a polarizing film with a high polarization degree is obtained.

[Chemical formula 2]

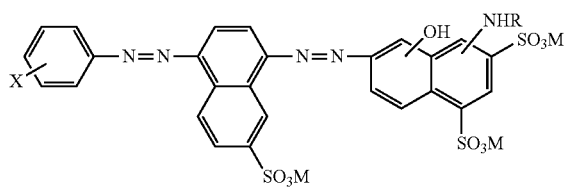

(2)

In the general formula (2), R is a hydrogen atom, an alkyl group having 1 to 3 carbon numbers, an acetyl group, a substituted or unsubstituted benzoyl group, or a substituted or unsubstituted phenyl group. X is a hydrogen atom, a halogen atom, a nitro group, a cyano croup, an alkyl group having 1 to 4 carbon numbers, an alkoxy group having 1 to 4 carbon numbers or a —$SO_3M$ group.

In the aforementioned general formula (2), M is a counterion. M is a hydrogen atom, an alkali metal atom, alkaline-earth metal atom or a metal ion before water-resistant treatment. After the water-resistant treatment, M represents partially or wholly cationic species derived from a nitrogen atom of an alicyclic structure-containing compound having at least two nitrogen atoms in the aforementioned molecule.

It is possible to obtain the azo compound represented by the aforementioned general formula (2) by diazotizing and coupling an aniline derivative and a naphthalene sulfonate derivative in accordance with a conventional method and the obtained monoazo compound is subject to diazotization and coupling reaction with an amino naphthol disulfonic acid derivative.

[Alicyclic Structure-Containing Compound]

The alicyclic structure-containing compound to be used in the present invention includes at least two nitrogen atoms in the molecule and increase resistance against water of the polarizing film by the interaction with anionic groups of the aforementioned organic dye. The phrase "an alicyclic structure-containing compound" means herein a compound which is configured to circularly bond any one of carbon atoms, nitrogen atoms, oxygen atoms, and sulfur atoms without a conjugated double bond. There may be a double bond in a ring in the aforementioned alicyclic structure when a conjugated double bond is not included in the alicyclic structure.

When compared to an aromatic ring structure-containing compound, in the aforementioned alicylic structure-containing compound, the distance between two nitrogen atoms is changeable. Accordingly, the compound is not easy to be separated from the organic dyes, resulting in improvement in water resistance.

The number of nitrogen atoms in the molecule of the aforementioned alicyclic structure-containing compound is preferably 2 to 10, more preferably 2 to 4. When the number of nitrogen atom is one, it is impossible to cross-link the organic dyes (intermolecular cross-linking). As a result, it is impossible to enhance water resistance of the polarizing film. On the contrary, when the number of nitrogen atoms is too great (for instance, over 10), the cross-linking between the organic dyes becomes too complicated and thereby there is a possibility that optical characteristics may be reduced due to poor uniformity in orientation of the organic dyes.

The aforementioned alicyclic structure-containing compound is preferably a monocyclic-based compound, more preferably cycloalkyl diamine with nitrogen atoms 5 to 7, piperazine, homopiperazine, 1,4-diazabicyclo (2,2,2) octane (DABCO), and sparteine or a mixture thereof. Examples of the aforementioned cycloalkyl diamine include 1,2-cyclohexane diamine, 1,4-cyclohexane diamine, 1,2-cyclopentane diamine or the like. It is possible to obtain a polarizing film having superior moisture resistance because these compounds are capable of maintaining a suitable distance among nitrogen atoms. Further, in the case where the aforementioned alicyclic structure-containing compound has a structural variant such as a cis body or a trans body, any one of them or a mixture thereof may be used.

The aforementioned alicyclic structure-containing compound is used in a state of a water solution (a water-resistant treatment liquid). The alicyclic structure-containing compound in the water-resistant treatment liquid preferably has a concentration of 5% by weight to 30% by weight, more preferably 10% by weight to 20% by weight.

[Process for Producing Water-Resistant Polarizing Film]

A process for producing a water-resistant polarizing film of the present invention includes a step of contacting a liquid (water-resistant treatment liquid) containing an alicyclic structure-containing compound having at least two nitrogen atoms in a molecule with a polarizing film including an organic dye having at least two anionic groups.

The process for producing a water-resistant polarizing film of the present invention is not particularly limited, but may include other steps as long as the process includes the aforementioned step. Examples of the other steps typically include a step of washing a surface of the polarizing film after contacting the water-resistant treatment liquid with the surface of the polarizing film to remove any extra water-resistant treatment liquid adhered to the surface of the polarizing film or a step of drying the surface of the polarizing film after contacting the water-resistant treatment liquid with the surface of the polarizing film.

The content of the organic dye included in the polarizing film before water-resistant treatment is preferably 80% by weight to 100% by weight, more preferably 90% by weight to 100% by weight relative to the total weight of the polarizing film. As described in Japanese Patent Application Laid-on Publication No. 2007-61755 A, it is possible to obtain such a polarizing film by casting by flow a coating solution containing an organic dye having anionic groups and a solvent and then orienting the organic dye.

The aforementioned polarizing film is not particularly limited as long as the polarizing film includes an organic dye having at least two anionic groups and may include any additives or other organic dyes. Examples of such an additive include a surfactant, an antioxidant, an antistatic agent, an ultraviolet absorber, and an antibacterial agent or the like.

The means for contacting the water-resistant treatment liquid with the surface of the aforementioned polarizing film is not particularly limited, but the water-resistant treatment liquid may be coated with the surface of the polarizing film, alternatively, the polarizing film may be immersed in the water-resistant treatment liquid.

[Applications]

The water-resistant polarizing film to be used in the present invention is preferably applied to liquid crystal panels, such as liquid crystal television units, liquid crystal displays, cell phones, digital cameras, video cameras, portable game devices, car navigation system, coping machines, printers, facsimile machines, watches, and microwave ovens or the like.

EXAMPLES

Example 1

In accordance with a conventional method ("Riron Seizo Senryo Kagaku" Fifth Edition (Theoretical production Dye Chemistry), Yutaka Hosoda (published on Jul. 15, 1968, GIHODO SHUPPAN Co., Ltd.), pages 135 to 152), a monoazo compound was produced by diazotizing and coupling 4-nitroaniline and 8-amino-2-naphthalene sulfonic acid. The obtained monoazo compound was diazotized by a conventional method in the same manner and was further subject to diazotization and coupling reaction with 1-amino-8-naphthol-2,4-disulfonate lithium salt to obtain a crude product and salting out was carried out with lithium chloride to obtain an azo compound having the following structural formula (3):

[Chemical formula 3]

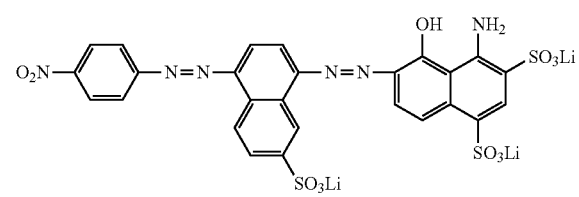

(3)

The azo compound of the aforementioned structural formula (3) was dissolved in ion-exchange water to prepare a coating solution exhibiting a nematic liquid-crystalline phase of 20% by weight. The coating solution was applied onto a norbornene-based polymer film (produced by Nippon Zeon Co., Ltd., product name: "Zeonor") with rubbing treatment and corona treatment using a bar coater (produced by BUSCHMAN, product name: "Mayerrot HS4") to form a polarizing film with a thickness of 0.4 µm (before water-resistant treatment) on a norbornene polymer film by natural drying in a temperature-controlled room at 23° C.

Next, the polarizing film was water-resistant treated by being immersed in a water solution (water-resistant treatment liquid) containing 10% by weight of piperazine (produced by Tokyo Chemical Industry Co., Ltd.) of the following structural formula (4). After washing by water, the polarizing film was dried naturally in a constant temperature room at 23° C.

to prepare a water-resistant polarizing film. Table 1 shows characteristics of the obtained water-resistant polarizing film.

[Chemical formula 4]

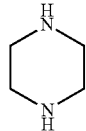

(4)

Piperazine

Example 2

A water-resistant polarizing film was prepared in the same manner as in Example 1 except for using 1,2-cyclohexane diamine of the following structural formula (4) (produced by Tokyo Kasei K.K.) as a substitute for piperazine. Table 1 shows characteristics of the obtained water-resistant polarizing film.

[Chemical formula 5]

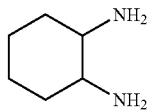

(5)

1,2-cyclohexane diamine

Comparative Example 1

A water-resistant polarizing film was prepared in the same manner as in Example 1 except for using melamine (produced by Tokyo Chemical Industry co., Ltd.) as a substitute for piperazine. Table 1 shows characteristics of the obtained water-resistant polarizing film.

Comparative Example 2

A polarizing film was prepared in the same manner as in Example 1 except for not conducting water-resistance treatment. Table 1 shows characteristics of the obtained polarizing film.

[Measuring Method]
[Measurement of Thickness]

A portion of a polarizing film was released to obtain the thickness of the polarizing film by measuring the level difference using a three-dimensional measurement system of the shape of a non-contact surface (manufactured by Ryoka Systems, Inc., product name: "Micromap MM5200").

[Observation of Liquid Crystal Phase]

A small amount of a coating solution was sandwiched by two pieces of slide glasses to observe liquid crystal phases using a polarization microscope (manufactured by Olympus, product name: "OPTIPHOT-POL").

[Evaluation of Water-Resistance]

A sample of the polarizing film was visually observed whether the polarizing film was maintained or dissolved when immersed in a water solution including a compound having a nitrogen atom.

[Measurement of Transmittance and Polarization Degree]

With the use of a spectrometer with Glan-Thompson Polarizer (produced by JASCO Corporation, U-4100), measured light of linear polarizer at a wavelength of 380 nm to 780 nm was allowed to enter to obtain average $K_1$ and $K_2$ of this wavelength region to calculate the following equation by multiplying a visibility correction factor for each wavelength to be integrated:

$$\text{Single transmittance}(T) = (k_1 + k_2)/2$$

$$\text{Polarization degree}(P) = (k_1 - k_2)/(k_1 + k_2)$$

wherein $k_1$ represents a transmittance of linear polarization in the maximum transmittance direction and $k_2$ represents a transmittance of linear polarization in a direction orthogonal to the direction of the maximum transmittance.

[Humidification Test]

A norbornene-based polymer film and a laminate of the water-resistant treated polarizing film were allowed to stand for 500 hours in a constant temperature device (produced by Espec Corp, Product name: PH-3KT) at humidity 90% RH, at a temperature of 60° C. to obtain an absolute value of a change rate by measuring the single transmittance and the polarization degree of the polarizing film before and after the test.

$$|\Delta T|(\%) = 100 \times |T(\text{after test}) - T(\text{before test})|/T(\text{before test})$$

$$|\Delta P|(\%) = 100 \times |P(\text{after test}) - P(\text{before test})|/P(\text{before test})$$

What is claimed is:

1. A water-resistant polarizing film comprising: an organic dye having at least two anionic groups; and an alicyclic structure-containing compound having at least two nitrogen atoms in a molecule, wherein the alicyclic structure-containing

TABLE 1

| | A compound contained in a water-resistant treatment liquid with at least two nitrogen atoms in a molecule | Water resistance O: a polarizing film is maintained after water resistant treatment x: a polarizing film is dissolved during the water-resistant treatment | \|ΔT\| (%) | \|ΔP\| (%) |
|---|---|---|---|---|
| Example 1 | Piperazine (Aicylclic structure) | O | 0.2 | 0.1 |
| Example 2 | 1,2-cyclohexane diamine (Alicyclic structure) | O | 1.6 | 0.2 |
| Comparative Example 1 | Melamine (Aromatic ring structure) | x | 5.3 | 1.1 |
| Comparative Example 2 | Nil | x | Unmeasurable (Dissolution of polarizing film) | Unmeasurable (Dissolution of polarizing film) | compound is selected from the group consisting of cycloalkyl diamine, piperazine, homopiperazine, 1,4-diazabicyclo (2,2,2) octane (DABCO), and sparteine, or a mixture thereof; wherein the water-resistant polarizing film exhibits absorption dichroism at least at one wavelength of 380 nm to 780 nm region; and the thickness of the water-resistant polarizing film is from 0.1 μ.m to 10 μ.m.

2. The polarizing film according to claim 1, wherein each of the anionic groups is selected from the group consisting of a sulfonic acid group, a carboxyl group, a phosphate group, and a base thereof.

3. The polarizing film according to claim 1, wherein the organic dye is an azo compound represented by the following general formula (2):

[Chemical formula 2]

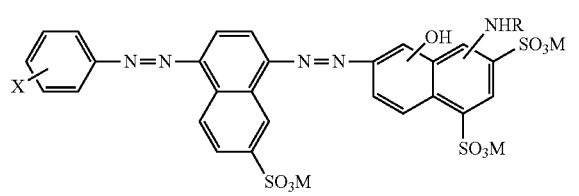

(2)

wherein R is a hydrogen atom, an alkyl group having 1 to 3 carbon numbers, an acetyl group, a substituted or unsubstituted benzoyl group, or a substituted or unsubstituted phenyl group. X is a hydrogen atom, a halogen atom, a nitro group, a cyano croup, an alkyl group having 1 to 4 carbon numbers, an alkoxy group having 1 to 4 carbon numbers, or a —$SO_3M$ group. M represents a counterion.

4. A process for producing a water-resistant polarizing film according to claim 1, comprising a step of contacting a liquid containing an alicyclic structure-containing compound having at least two nitrogen atoms in a molecule with a polarizing film including an organic dye having at least two anionic groups.

5. The polarizing film according to claim 1, wherein the alicyclic structure-containing compound has been incorporated into the polarizing film via a surface thereof including the organic dye.

6. The polarizing film according to claim 1, wherein the organic dye is cross-linked with the alicyclic structure-containing compound.

* * * * *